United States Patent
Takahashi et al.

(10) Patent No.: US 8,270,703 B2
(45) Date of Patent: Sep. 18, 2012

(54) DEFECT INSPECTION APPARATUS, DEFECT INSPECTION METHOD, AND MANUFACTURE METHOD FOR SEMICONDUCTOR DEVICE

(75) Inventors: Naohiro Takahashi, Shinjuku-ku (JP); Isao Motomura, Shinjuku-ku (JP)

(73) Assignee: Fujitsu Semiconductor Limited, Yokohama (JP)

( * ) Notice: Subject to any disclaimer, the term of this patent is extended or adjusted under 35 U.S.C. 154(b) by 525 days.

(21) Appl. No.: 12/404,430

(22) Filed: Mar. 16, 2009

(65) Prior Publication Data
US 2009/0304261 A1 Dec. 10, 2009

(30) Foreign Application Priority Data

Jun. 10, 2008 (JP) .................................. 2008-151764
Nov. 27, 2008 (JP) .................................. 2008-302214

(51) Int. Cl.
*G06K 9/00* (2006.01)

(52) U.S. Cl. ........ 382/149; 382/141; 382/145; 382/209; 382/218; 356/237.2; 356/237.4; 356/237.1

(58) Field of Classification Search .................. 382/141, 382/145, 147, 149, 209, 218; 356/237.1–237.5
See application file for complete search history.

(56) References Cited

U.S. PATENT DOCUMENTS

| 6,661,507 B2 * | 12/2003 | Yoda et al. | 356/237.2 |
| 6,941,009 B2 * | 9/2005 | Wienecke | 382/145 |
| 2005/0119850 A1 | 6/2005 | Asano | |
| 2008/0063258 A1 * | 3/2008 | Kimba | 382/149 |

FOREIGN PATENT DOCUMENTS

| JP | 2002-228606 A | 8/2002 |
| JP | 2004-281482 A | 10/2004 |
| JP | 2005-101224 | 4/2005 |

* cited by examiner

*Primary Examiner* — Gregory J Toatley
*Assistant Examiner* — Iyabo S Alli
(74) *Attorney, Agent, or Firm* — Westerman, Hattori, Daniels & Adrian, LLP

(57) ABSTRACT

A distinguishing size for distinguishing a pseudo defect from a defect caused by a process trouble is stored in a first storage area. Defect data are stored in a second storage area. A processing unit detects a defect on a wafer surface, and stores the defect data in the second storage area. Before a defect detection process is completed for all areas of the wafer surface, a size of a defect detected in a partial area is compared with the distinguishing size stored in the first storage area. If the detected defect has a size equal to or larger than the distinguishing size, an alarm is output through an output unit, whereas if a defect having a size equal to or larger than the distinguishing size is not detected, the defect detection process is executed for the area still not subjected to the defect detection process.

12 Claims, 13 Drawing Sheets

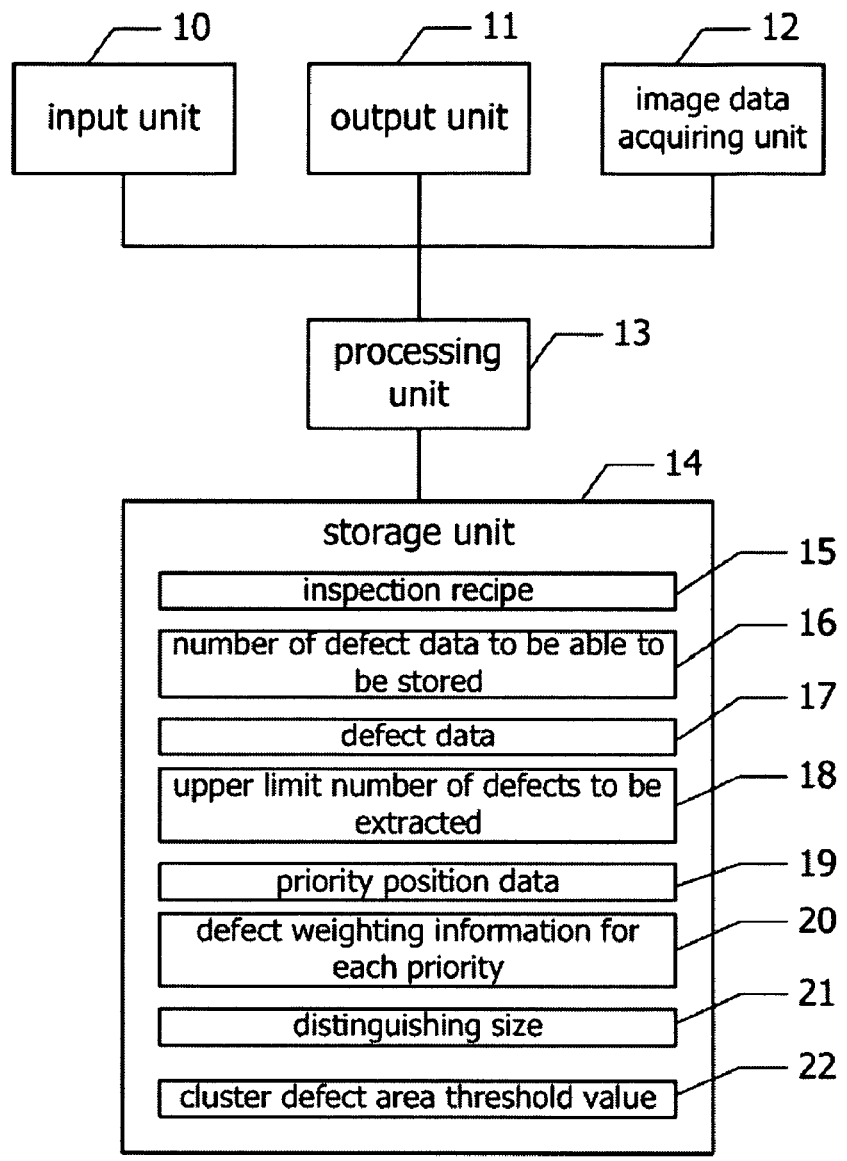

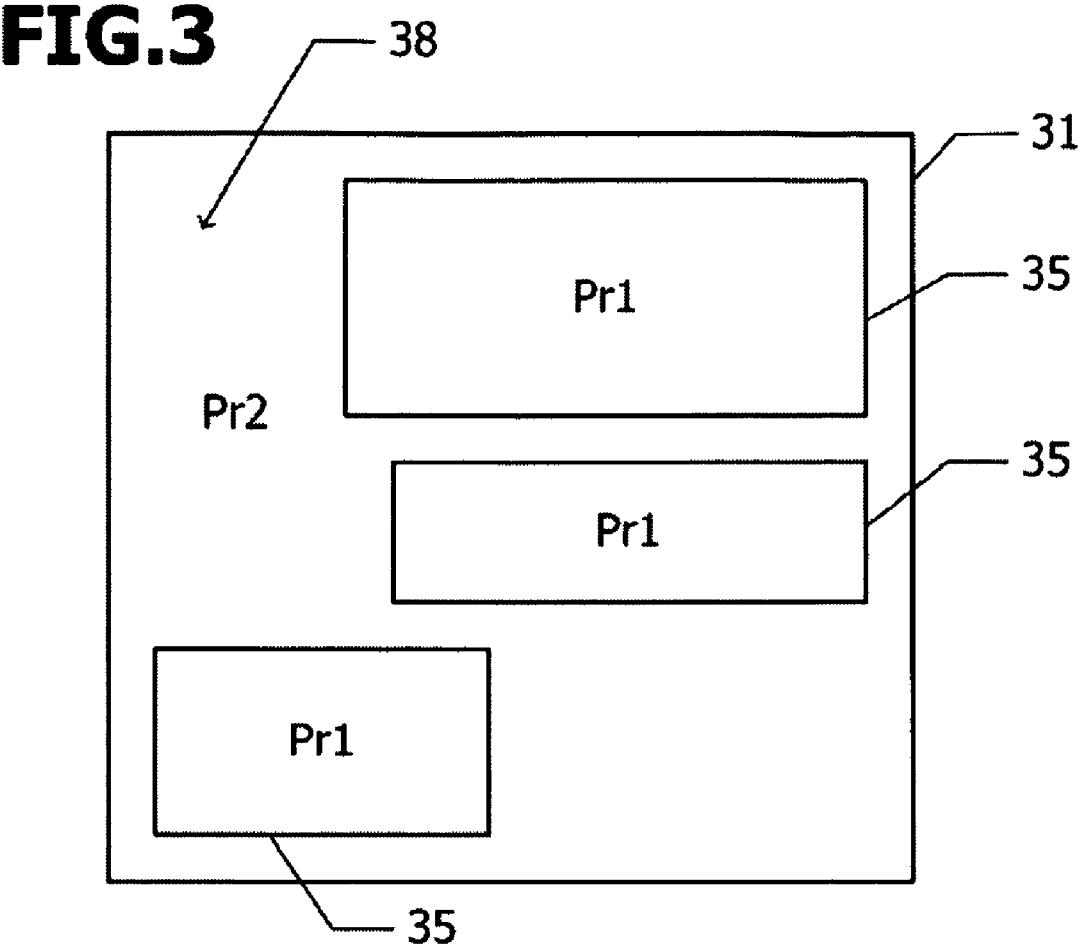

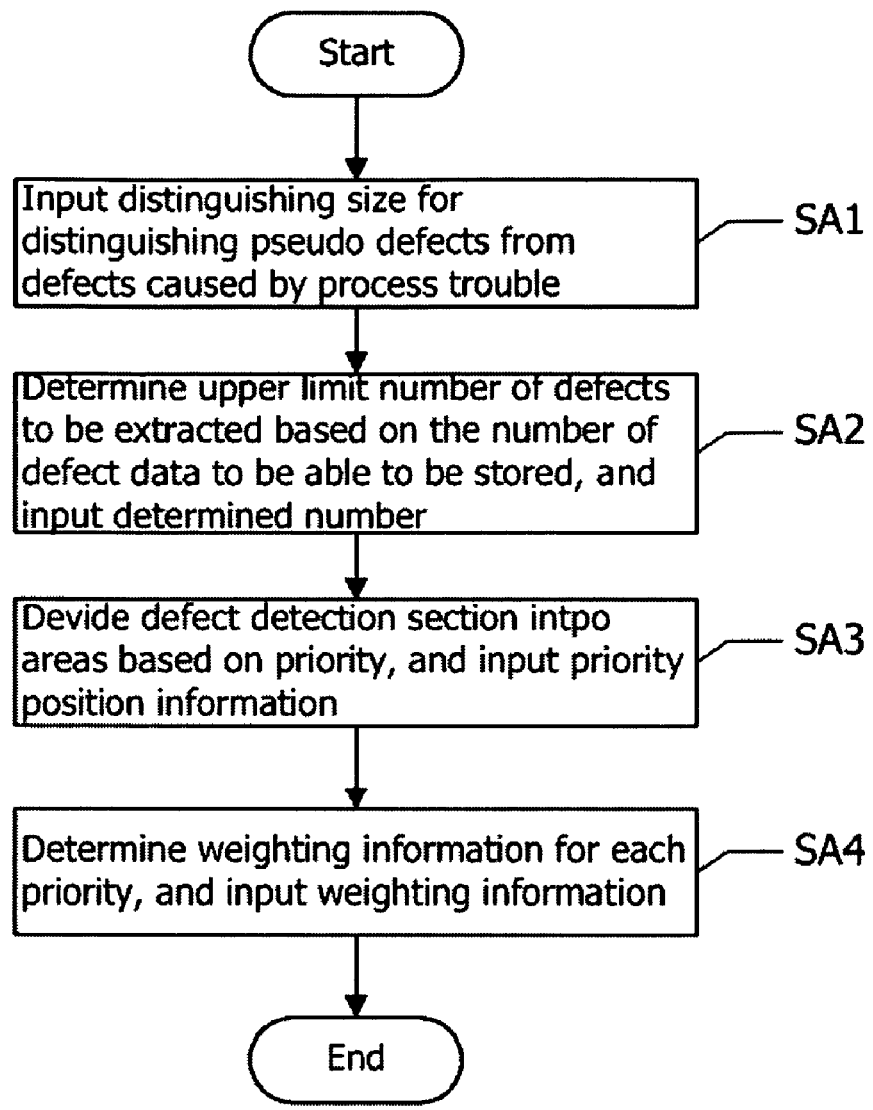

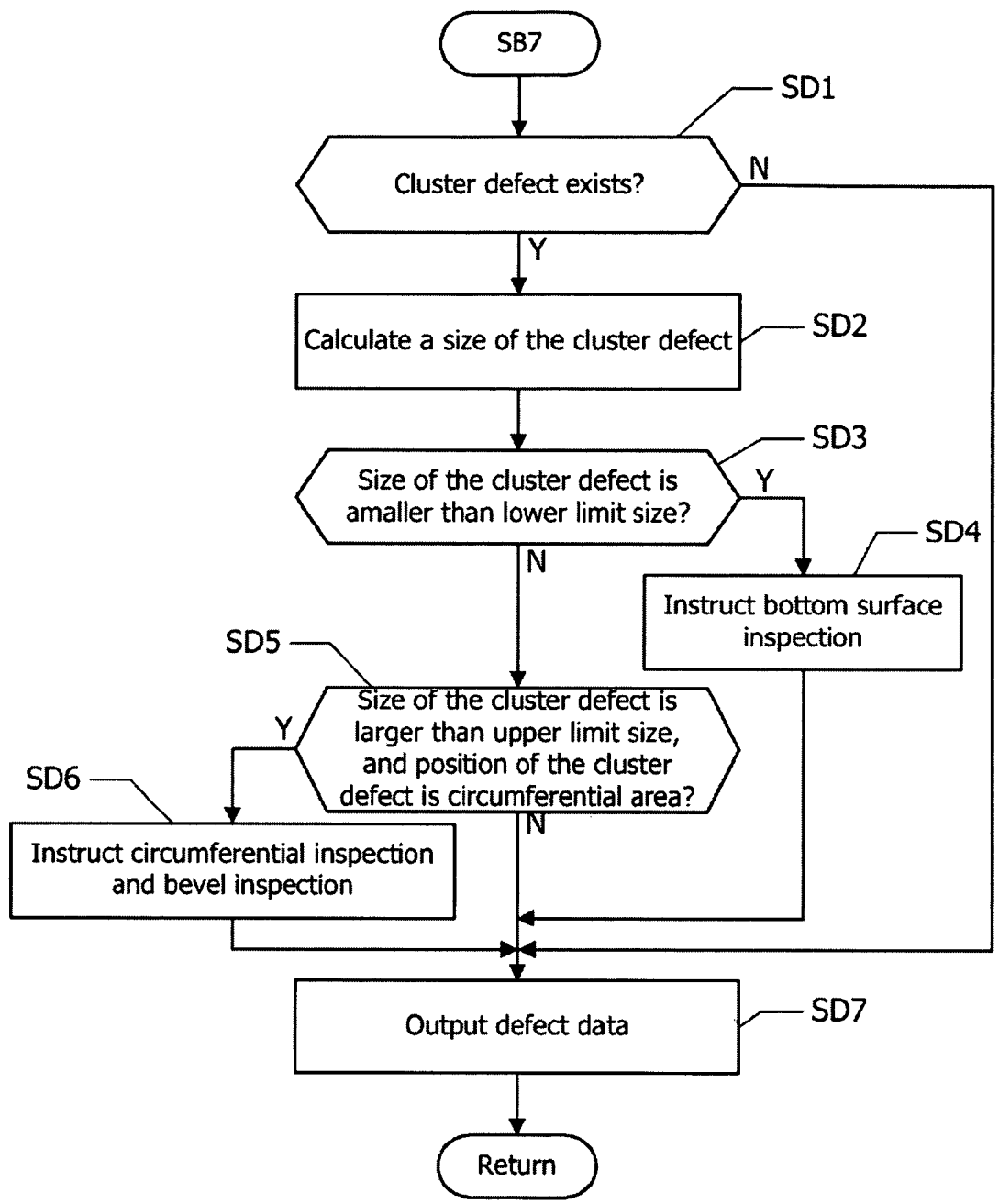

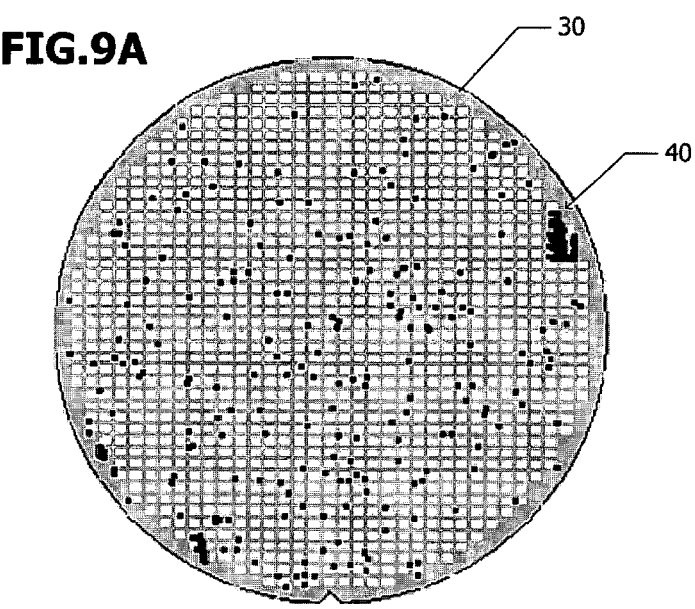
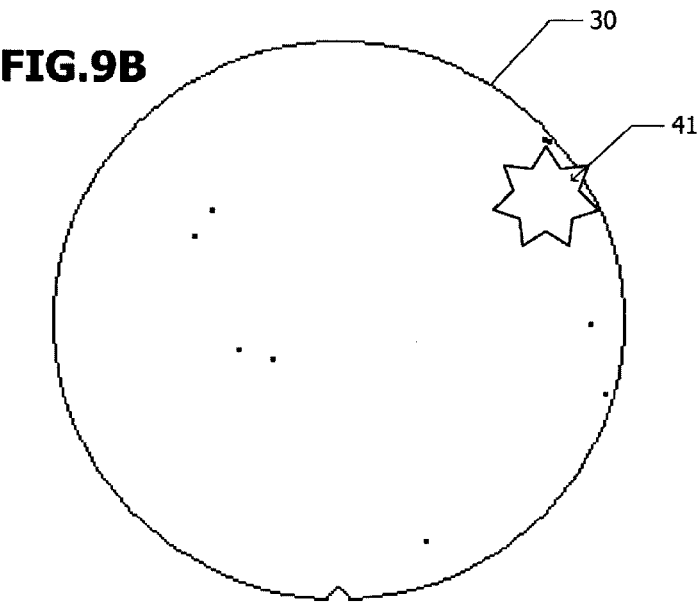

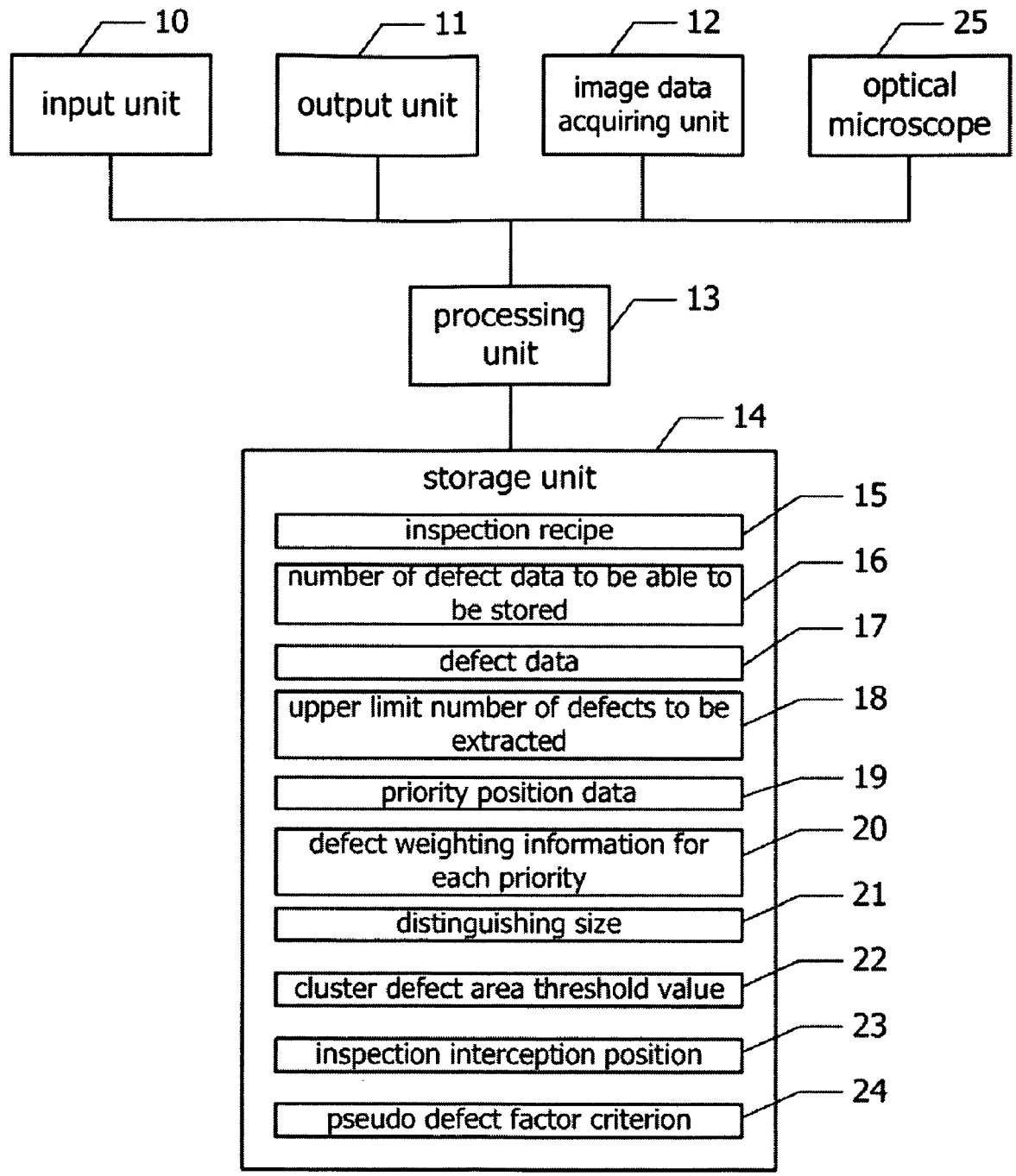

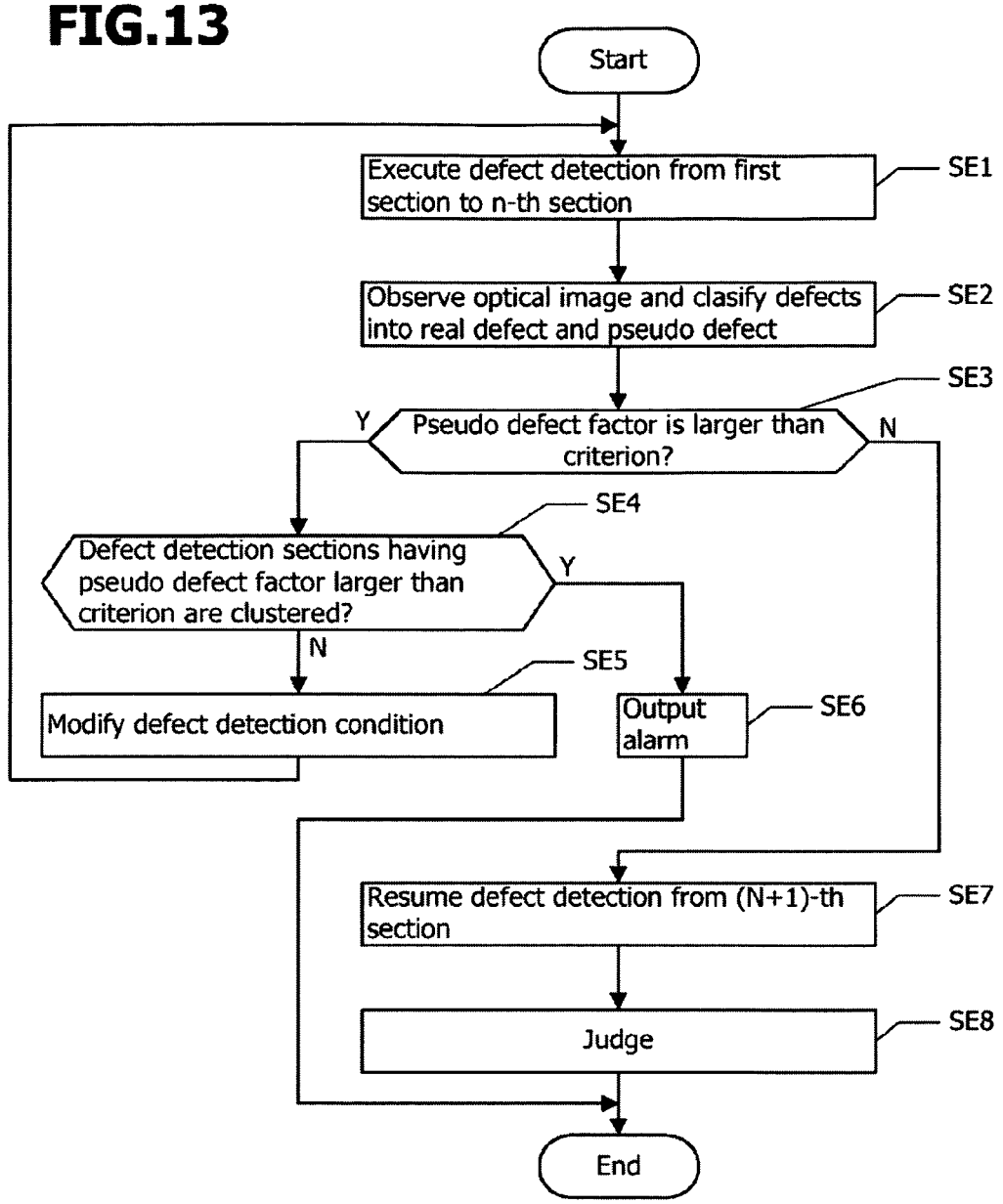

DEFECT INSPECTION APPARATUS, DEFECT INSPECTION METHOD, AND MANUFACTURE METHOD FOR SEMICONDUCTOR DEVICE

CROSS-REFERENCE TO RELATED APPLICATIONS

This application is based upon and claims the benefit of priority of the prior Japanese Patent Applications No. 2008-151764, filed on Jun. 10, 2008, and No. 2008-302214, filed on Nov. 27, 2008 the entire contents of which are incorporated herein by reference.

FIELD

The embodiments discussed herein are related to a defect inspection apparatus, a defect inspection method, and a manufacture method for a semiconductor device utilizing the defect inspection method.

BACKGROUND

In a manufacturing process for a semiconductor integrated circuit device, inspection is performed whether there is any pattern defect to be caused by unsatisfactory exposure or position misalignment and a detect to be caused by particles deposited on a wafer surface. The number of defects whose defect data can be stored is limited dependent upon a storage capacity of a defect inspection apparatus. When the number of defects exceeds this limit during defect detection, the defect detection process stops. As a result, defect data on defects over the whole surface of a wafer cannot be acquired.

A method is publicly known by which an upper limit value of the number of detected defects per chip on a wafer is set in advance. According to this method, when the number of detected defects reaches the upper limit value, inspection of the chip is discontinued, and the next chip is inspected. It is therefore possible to inspect all chips on a wafer.

SUMMARY

Defects are generally detected through comparison between wafer surface image data and reference image data or between image data of two areas on a wafer surface having the same pattern. If an alignment precision of image data lowers because of insufficient adjustment of a defect inspection apparatus, position displacement during inspection is detected as a defect even if the defect is not generated during the process. Such a defect is called a "pseudo defect". A conventional apparatus cannot distinguish a pseudo defect from a defect generated during a process.

According to an aspect of an embodiment, a defect inspection apparatus includes:
a distinguishing size storage unit for storing a distinguishing size of defect for distinguishing between a defect caused by a process and a pseudo defect not caused by the process;
an image data acquiring apparatus for acquiring image data of a surface of a wafer to be inspected;
a defect information storage unit for storing information on a plurality of detected defects;
an output apparatus for outputting inspection results; and
a processing apparatus,
wherein,
the processing apparatus detects a defect on a wafer surface in accordance with image data acquired by the image data acquiring apparatus; makes the defect information storage unit store information on the detected defect;
compares a size of a defect detected in a partial area with the distinguishing size stored in the distinguishing size storage unit before a defect detection process is completed for a whole area of the wafer surface to be subjected to defect detection; makes the output apparatus output an alarm notifying that the inspection apparatus is abnormal, if a defect is detected having a size not smaller than the distinguishing size; and executes the defect detection process for the area still not subjected to the defect detection process, if a defect is not detected having a size not smaller than the distinguishing size.

BRIEF DESCRIPTION OF DRAWINGS

FIG. 1 is a block diagram of a detect inspection apparatus according to a first embodiment.

FIG. 3 is a diagram illustrating a layout in a defect detection section.

FIG. 4 is a flow chart illustrating an inspection preparatory stage.

FIG. 8 is a detailed flow chart of Step SB7 of the defect inspection method of the first embodiment.

FIG. 9A is a plan view of a semiconductor wafer illustrating an example of distribution of defects, and FIG. 9B is a diagram illustrating the bottom surface of the wafer.

FIG. 11 is a block diagram of a defect inspection apparatus according to a second embodiment.

FIG. 13 is a flow chart illustrating a defect inspection method according to the second embodiment.

DESCRIPTION OF EMBODIMENTS

Figure 2A:
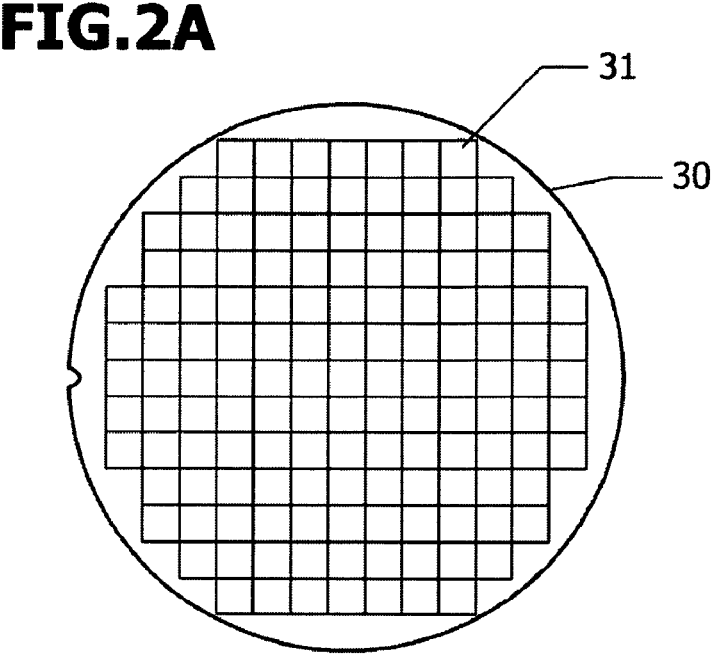
FIG. 2A is a plan view of a semiconductor wafer to be inspected.

Embodiments will now be described with reference to the accompanying drawings.

First Embodiment

FIG. 1 is a block diagram of a defect inspection apparatus according to the first embodiment. The defect inspection apparatus includes an input unit 10 an output unit 11, an image data acquiring unit 12, a processing unit 13, and a storage unit 14. An operator inputs data to the defect inspection apparatus through the input unit 10. Inspection results and various alarms are output from the output unit 11. The image data acquiring unit 12 acquires image data of the surface of a semiconductor wafer to be inspected. A bright-field microscope, a dark-field microscope or the like are used as the image data acquiring unit 12. The storage unit 14 ensures an area for storing various data to be used for defect detection, an area for storing inspection results and other areas.

FIG. 2A is a plan view of a semiconductor wafer 30 to be inspected. A plurality of chips disposed in a matrix shape are defined on the surface of the semiconductor wafer 30 to be inspected. For example, one chip corresponds to a unit area 31 for defect detection. An area as the unit for defect detection is called a "defect detection section".

Figure 2B:
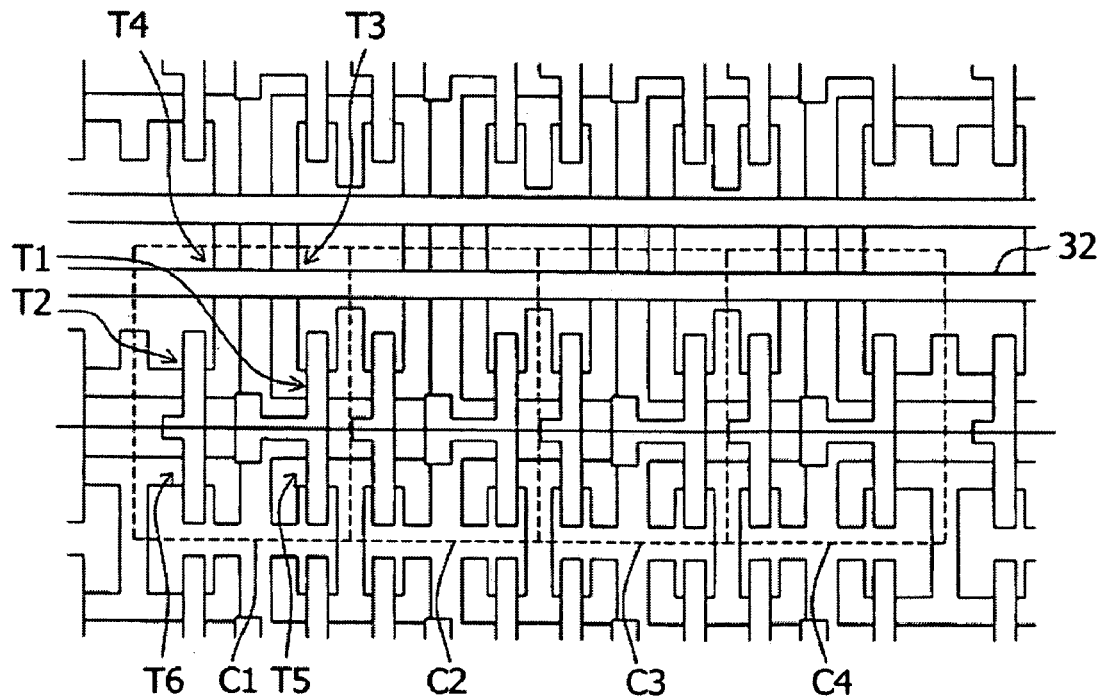
FIG. 2B is a plan view of illustrating an example of an electronic circuit pattern formed on a semiconductor wafer.

As illustrated in FIG. 2B, electronic circuit patterns are formed in each chip. For example, each of SRAM cells C1 to C4 includes six MOS transistors T1 to T6. Gate electrodes of the MOS transistors T3 and T4 extend laterally in FIG. 2B to double as a word line 32. The electronic circuit patterns formed on the semiconductor wafer 30 to be inspected may be DRAM patterns, logic circuit patterns or the like, instead of SRAM patterns.

FIG. 3 illustrates an example of the layout of electronic circuit patterns in one defect inspection section 31. Memory cell areas 35 are defined in the defect inspection section 31. An area other than the memory cell areas 35 is a logic circuit area 38. Patterns in the memory cell areas 35 are denser than patterns in the logic circuit area 38. Therefore, even a smaller defect affects greatly the operation of an electronic circuit. It is therefore preferable that a priority of defect detection in the memory cell areas 35 is set higher than a priority of defect detection in the logic circuit area 38.

As described above, areas Pr1 and an area Pr2 are defined in the defect detection section 31, priority for defect detection of the areas Pr1 being higher than that of the areas Pr2. In the example illustrated in FIG. 3, although the memory cell areas 35 are set as the high priority areas Pr1 and the logic circuit area 38 is set as the low priority area Pr2, the priority may be determined in accordance with other information. For example, the priority is preferably determined in accordance with a dense/coarse degree of patterns.

Instead of classifying the priority into two degrees: high and low, the priority may be classified into three priority degrees: high, middle and low.

Description continues by reverting to FIG. 1. The storage unit 14 ensures a storage area 15 for storing an inspection recipe, storage area 16 for storing number of pieces of defect data to be able to be stored, a storage area 17 for storing defect data, a storage area 18 for storing upper limit number of defects to be extracted, a storage area 19 for storing priority position information, a storage area 20 for storing defect weighting information for each priority, a storage area 21 for storing distinguishing size, a storage area 22 for storing cluster defect area threshold value and the like. Each of "pieces of defect data" corresponds to a detected defect.

The storage area 15 stores an inspection recipe for each product type of a semiconductor wafer and for each process. The storage area 17 stores defect data of detected defects. Since a capacity of the storage area 17 is finite, the number of pieces of defect data to be able to be stored is limited. The number of pieces of defect data to be able to be stored per one semiconductor wafer is stored in the storage area 16.

In the first embodiment, not only the number of pieces of defect data to be able to be stored per one semiconductor wafer but also an upper limit number of defects to be extracted per one defect detection section 31 are determined. This upper limit number is stored in the storage area 18.

The storage area 19 stores priority position information for correlating a position on the wafer surface to a priority. More specifically, stored is information which defines the positions of a high priority area Pr1 and a low priority area Pr2 in one defect detection section 31. For example, it is possible to determine whether the defect is in the high priority area Pr1 or in the low priority area Pr2 based on the position of a detected defect. The storage area 20 stores weighting information to be assigned to a defect in the high priority area Pr1 and a defect in the low priority area Pr2.

The storage area 21 stores a distinguishing size, e.g., an area for distinguishing between a defect caused by a process trouble and a pseudo defect. The processing unit 13 compares a piece of image data with another piece of image data to detect defects, in accordance with the image data acquired by the image data acquiring unit 12. For example, one piece of image data is ideal reference image data having no defect, and another piece of image data is actual image data of the surface of the semiconductor wafer. Alternatively, two pieces of image data of two areas of a semiconductor wafer having the same pattern may be compared with each other.

If there is a position displacement when two pieces of image data are compared, there is a difference between two pieces of image data, and this difference is detected as a defect (pseudo defect). Generally, a size of a pseudo defect is considerably larger than that of a defect caused by a process trouble. The storage area 21 stores a value larger than the maximum size of a defect caused by a general process trouble and smaller than a size of a general pseudo defect. A size of a detected defect is compared with the distinguishing size stored in the storage area 21 so that it is possible to determine whether the defect is the one caused by a process trouble or a pseudo defect.

The storage area 22 stores a lower limit threshold value and an upper limit threshold value.

FIG. 4 is a flow chart illustrating a preparatory stage before a defect inspection is performed. At initial settings of the apparatus, necessary data are stored in the storage area 15 for storing an inspection recipe and storage area 16 for storing number of pieces of defect data to be able to be stored.

At step SA1, an operator inputs a distinguishing size for distinguishing a defect caused by a process trouble and a pseudo defect through the input unit 10. The input distinguishing size is stored in the storage area 21.

At step SA2, the operator determines an upper limit number of defects to be extracted per one defect detection section 31 based on the number of pieces of defect data to be able to be stored dependent upon the inspection apparatus. The operator inputs the determined upper limit number of defects to be extracted through the input unit 10. The input number is stored in the storage area 18. Instead of input by the operator, the upper limit number of defects to be extracted per one defect detection section 31 may be calculated automatically based on the number of pieces of defect data to be able to be stored per one wafer. For example, a number obtained by dividing the number of pieces of defect data to be able to be stored by the number of defect detection sections 31 may be used as the upper limit number of defects to be extracted per one defect detection section 31. For example, if the number of defects to be able to be stored per one wafer is 120,000 and the number of defect detection sections 31 defined in one wafer is 600, the upper limit number of defects to be extracted per one defect detection section 31 is 200.

At step SA3, the defect detection section 31 is divided into a high priority area and a low priority area. The operator inputs this division result through the input unit 10. Input information is stored in the storage unit 19 for storing priority position information.

At step SA4, defect weighting is performed for each priority. As an example, a ratio of weight of defects in the high priority area Pr1 to weight of defects in the low priority area Pr2 is set to 9:1. The operator inputs the weight values through the input unit 10. The input values are stored in the storage area 20 for storing defect weighting information for each priority. This weighting information is used when some defects are extracted from detected defects.

The above-described information may be stored beforehand in the storage area 15 as a parameter of an inspection recipe.

Figure 5:
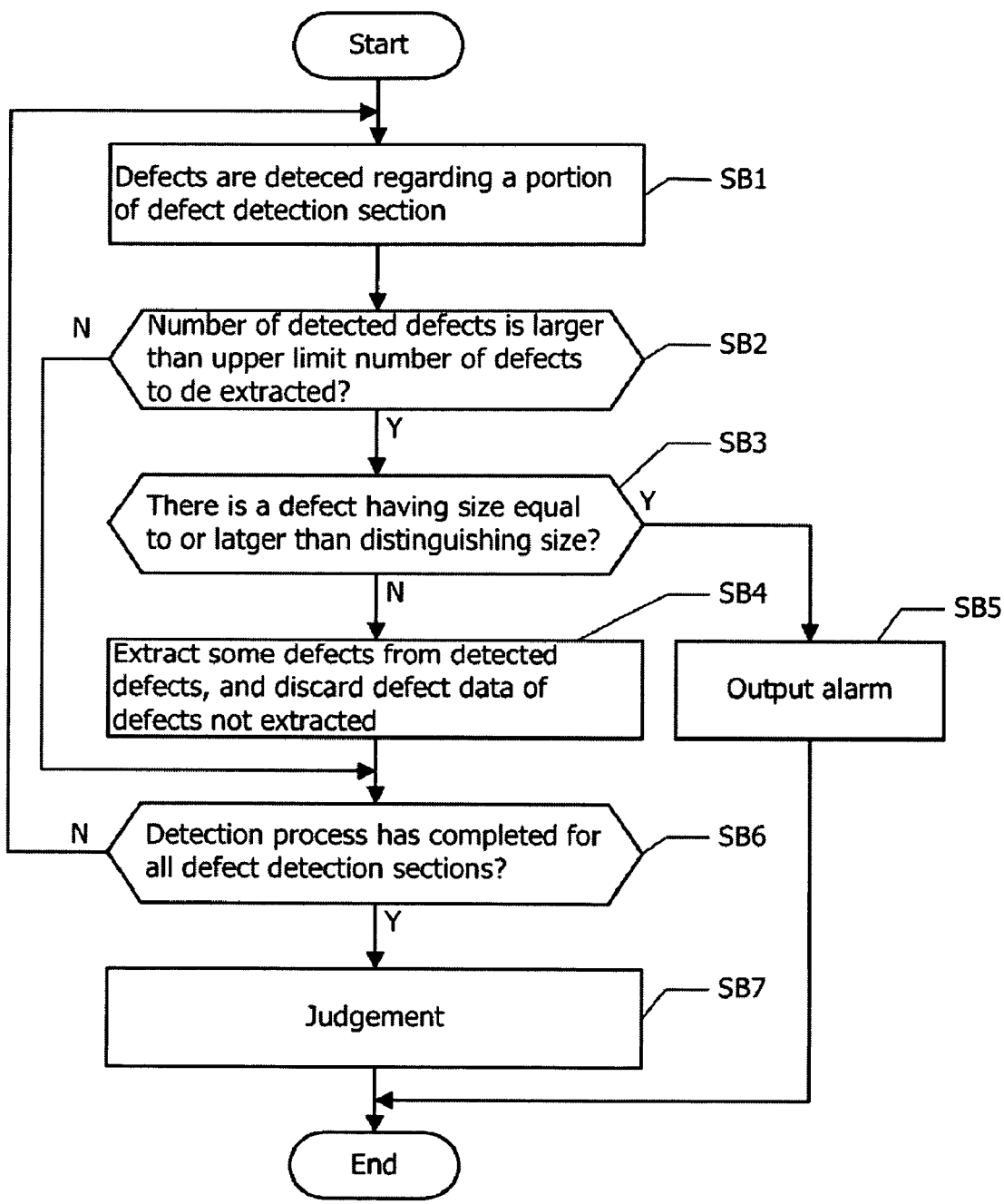
FIG. 5 is a flow chart illustrating a defect inspection method of the first embodiment.

FIG. 5 is a flow chart illustrating a defect inspection method according to the first embodiment. Each Step illustrated in FIG. 5 is executed by the processing unit 13.

At step SB1, image data of a semiconductor wafer to be inspected is acquired, and a defect detection process is executed for a portion of defect detection sections 31, e.g., one defect detection section 31. The defect detection process may be executed not for one detect detection section 31 but for a plurality of defect detection sections 31. For example, the defect detection process may be executed for defect detection sections 31 of one swath (one row) or two swaths.

Figure 6:
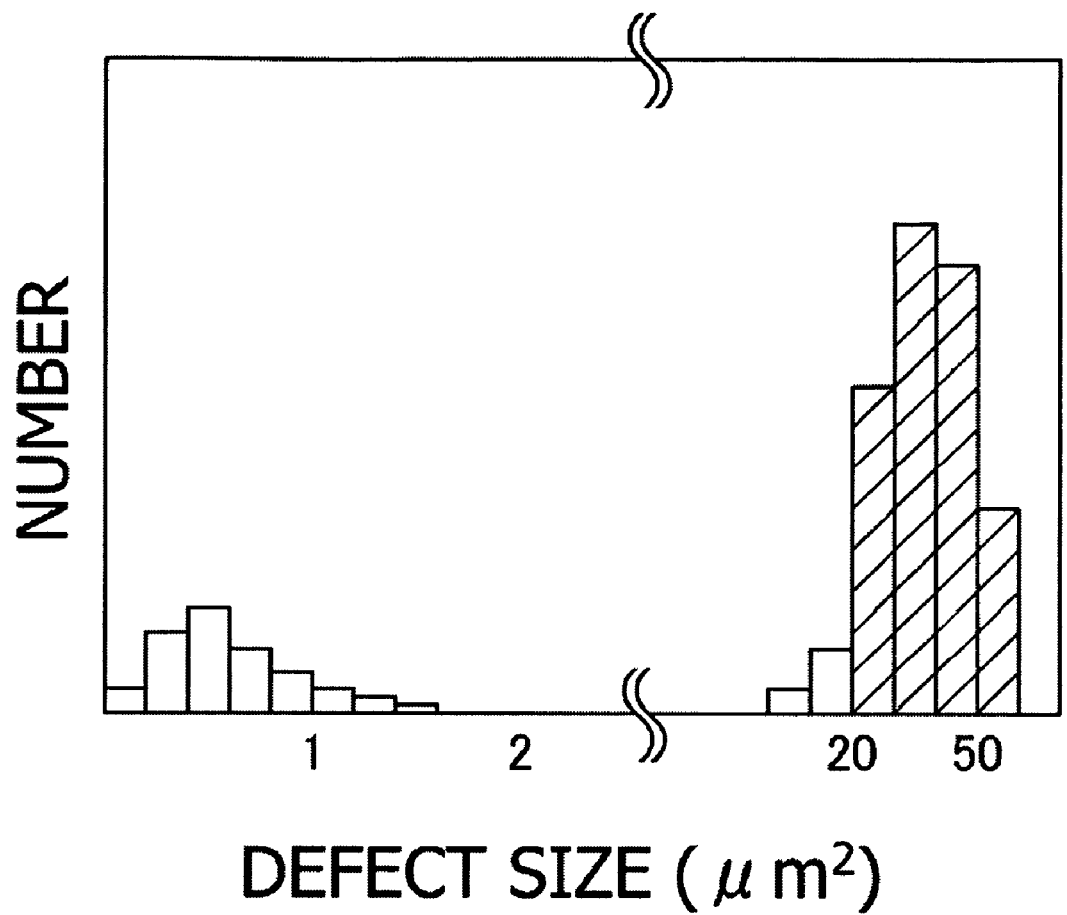
FIG. 6 is a histogram classifying detected defects by size.

FIG. 6 illustrates an example of a histogram of detected defects classified by size. The abscissa represents a defect size in the unit of "$\mu m^2$", and the ordinate represents the number of defects.

At step SB2, it is judged whether the number of detected defects is larger than the upper limit number of defects to be extracted. If one defect detection section 31 is used as the target of the defect detection process, the upper limit number of defects to be extracted as the comparison reference is equal to the number stored in the storage area 18 for storing the number of defects to be extracted. If the number of defect detection sections 31 as the target of the defect detection process is n, the upper limit number of defects to be extracted as the comparison reference is n times the number stored in the storage area 18. More in general, the upper limit number of defects to be extracted is calculated in accordance with the size of a target area of a defect detection process (the number of defect detection sections 31) and the number of pieces of defect data to be able to be stored in the storage area 16.

If the number of detected defects is larger than the upper limit number of defects to be extracted, step SB3 is executed, whereas if the number of detected defects is equal to or smaller than the upper limit number of defects to be extracted, step SB6 is executed.

At step SB3, it is judged whether a defect having a size equal to or larger than the distinguishing size stored in the storage area 21 exists or not in the detected defects. For example, the distinguishing size is set to 20 $\mu m^2$. The sizes of defects classified in the hatched portions in FIG. 6 are equal to or larger than the distinguishing size. If a defect having the size equal to or larger than the distinguishing size is detected, an alarm is issued from the output unit 11 at step SB5, and the defect inspection is terminated.

Detecting a defect having a size equal to or larger than the distinguishing size means that there is a position alignment failure of two pieces of image data for defect detection. Generally, as the position alignment failure occurs, a large number of pseudo defects are detected. If the defect detection process continues further for the defect detection section 31, a large number of pseudo defects are detected. The number of detected defects exceeds therefore the number of pieces of defect data to be able to be stored, and the inspection stops.

As the alarm is issued, the operator regulates again the inspection apparatus. By outputting the alarm and notifying the operator of occurrence of a position alignment failure, it becomes possible to prevent wasteful detection operations by using an inspection apparatus with insufficient regulation.

If it is judged at step SB3 that a defect having a size equal to or larger than the distinguishing size is not detected, then at step SB4 some defects are extracted from the detected defects, and defect data on the extracted defects are stored in the storage area 17. Defect data on the defects not extracted are discarded without being stored in the storage area 17. The details of step SB4 will be later described with reference to FIG. 7.

It is judged at step SB6 whether the defect detection process has been completed for all defect detection sections 31. If there remains a defect detection section 31 still not subjected to the detect detection process, the process returns to step SB1 and continues for the detection section 31 still not subjected to the detect detection process. If the defect detection process has been completed for all defect detection sections 31, the inspection results are Judged at step SB7. The details of step SB7 will be described later with reference to FIG. 8.

Figure 7:
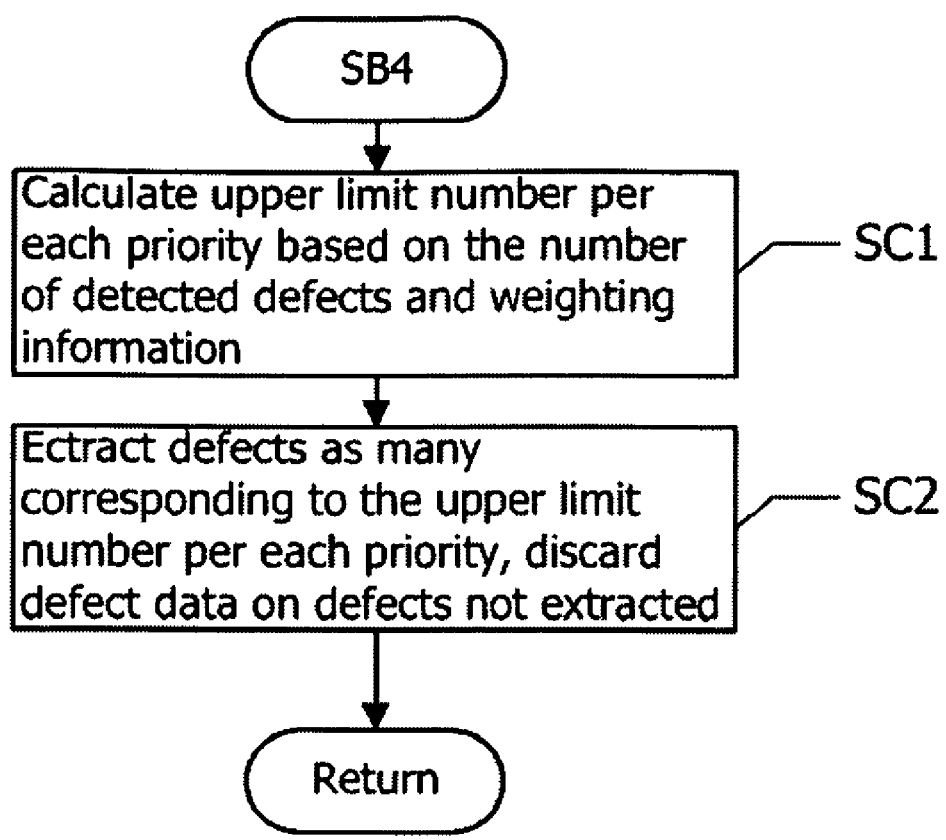
FIG. 7 is a detailed flow chart of Step SB4 of a defect inspection method of the first embodiment.

FIG. 7 is a detailed flow chart illustrating step SB4 of the flow chart in FIG. 5. First, at step SC1, in accordance with the number of all detected defects, position information of priority, and weighting information of each priority, the upper limit number of defects to be extracted for each priority is calculated. A sum of the upper limit number of defects to be extracted in the high priority area Pr1 and the upper limit number of defects to be extracted in the low priority area Pr2 is equal to the upper limit number of defects to be extracted used at step SB2 in FIG. 5. It is arranged that a defect is extracted from detected defects in the high priority area Pr1 at a larger probability than from detected defects in the low priority area Pr2. A specific example of extraction will be described below.

The weighting information stored in the storage area 20 is assumed to be (high priority area):(low priority area)=9:1. It is further assumed that the upper limit number of defects to be extracted per one defect detection section 31 is 200, the number of defect detection sections 31 for the defect detection target is one, and the number of actually detected defects is 700. Of the detected defects, it is assumed that 500 defects are in the high priority area Pr1, and 200 defects are in the low priority area Pr2. Since a weight of the high priority area Pr1 is nine times that of the low priority area Pr2, a ratio of the number of defects extracted from the detected defects in the high priority area Pr1 to the number of defects extracted from detected defects in the low priority area Pr2 is set to (500×9):(200×1). The total number of extracted defects is 200. Namely, nine defects are extracted from detected defects in the low priority area Pr2, and 191 defects are extracted from detected defects in the high priority area Pr1.

At step SC2, defects are extracted from the detected defects, the number of extracted defects being equal to the number calculated at step SC1. Data on the extracted defects are stored in the storage area 17, and data on defects not extracted are discarded.

With this method, the number of pieces of defect data per one defect detection section 31 stored in the storage area 17 is equal to or smaller than the upper limit number of defects to be extracted. Therefore, during inspection of a semiconductor wafer 30, the number of pieces of defect data stored in the storage area 17 will not excess the number of pieces of defect data to be able to be stored. Accordingly, defect data for all defect detection sections 31 of one semiconductor wafer 30 can be acquired.

Conventionally, when the number of detected defects reaches the number of pieces of defect data to be able to be stored, inspection stops halfway. Therefore, although defect data of a partial area of a semiconductor wafer can be obtained, defect data of an area still not subjected to the defect detection process cannot be obtained at all. In the above-described first embodiment, defect data of all defect detection sections 31 can be acquired although some defect data are discarded during inspection.

Further, by extracting defects in accordance with the priority, it is possible to suppress an inspection precision from being lowered by discarding some defect data.

FIG. 8 is a detailed flow chart illustrating step SB7 of the flow chart in FIG. 5. First, it is Judged at step SD1 whether a cluster defect exists or not. If a cluster defect does not exist, defect data are output from the output unit 11 at step S17. If a cluster defect exists, an area of the cluster defect is calculated at step SD2. The "area of a cluster defect" used herein means an area of a region where defects are aggregated. For example, in an example shown in FIG. 9A, a cluster defect 40 can be observed, and in an example shown in FIG. 10A, a cluster defect 45 can be observed.

It is judged at step S53 whether an area of the cluster defect is equal to or smaller than the lower limit threshold value stored in the storage unit 22. If the area of the cluster defect is equal to or smaller than the lower limit threshold value, the operator is urged via the output unit 11 to inspect a bottom surface, at step SD4. Thereafter, defect data are output at step SD7.

An example of FIG. 9A illustrates the case where the area of the cluster defect 40 is equal to or smaller than the lower limit threshold value. In this case, as illustrated in FIG. 9B, a focus failure in a photolithography process occurs often because of attachment of a foreign matter in an portion 41 corresponding to the cluster defect 40. As the bottom surface inspection is instructed from the output unit 11, the operator inspects whether particles are attached or not to the subject portion on the bottom surface of the semiconductor wafer under inspection.

If it is judged at step SD3 that the area of the cluster defect is not smaller than the lower limit threshold value, then it is judged at step SD5 whether the area of the cluster defect is equal to or larger than the upper limit threshold value and the position of the cluster defect is near the edge of the wafer. If the area of the cluster defect is equal to or larger than the upper limit threshold value and the position thereof is near the edge of the wafer, the operator is instructed via the output unit 11 to inspect the wafer circumferential area and bevel at step SD6. Thereafter, defect data are output at step SD7.

Figure 10A:
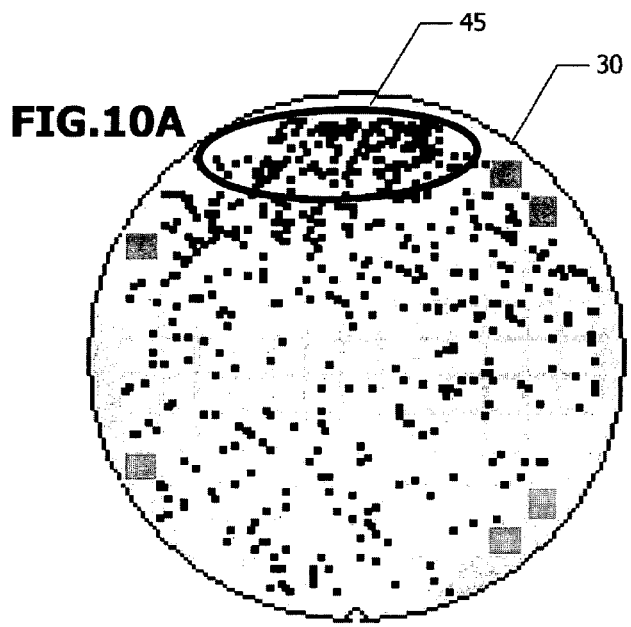
FIG. 10A is a plan view of a semiconductor wafer illustrating an example of distribution of defects.
Figure 10B:
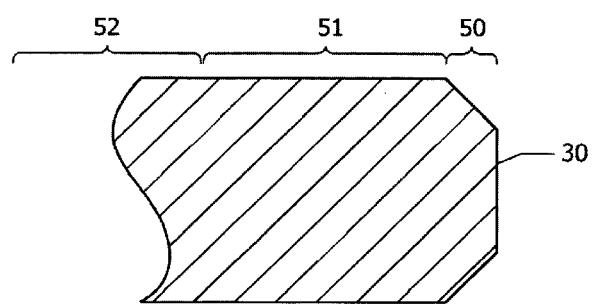
FIG. 10B is a cross sectional view illustrating a region near a wafer edge.

For example, the cluster defect 45 illustrated in FIG. 10A satisfies the conditions of step SD5. In this case, it is effective that an unused area 51 near the edge of the wafer and a bevel area 50 illustrated in FIG. 10B are inspected. The "unused area 51" is a flat region outside an effective area 52 assigned to chips in which electronic circuit patterns are formed. The "bevel area 50" means a slanted surface coupling a flat surface and an end surface perpendicular to the flat plane, in the wafer circumferential area.

By urging the operator to perform the wafer bottom surface inspection, circumferential area inspection, bevel inspection and the like, proper additional inspections can be performed even if the operator does not have sufficient skill.

Second Embodiment

FIG. 11 is a block diagram of a defect inspection apparatus according to the second embodiment. A storage area 23 for storing detect interception position and a storage area 24 for storing a pseudo defect factor criterion are added to the storage unit 14 of the defect inspection apparatus of the first embodiment illustrated in FIG. 1. The defect inspection apparatus includes further an optical microscope 25. The optical microscope 25 acquires an optical image at the designated position on a semiconductor wafer, under control of the processing unit 13, and transmits optical image data to the processing unit 13.

Figure 12:
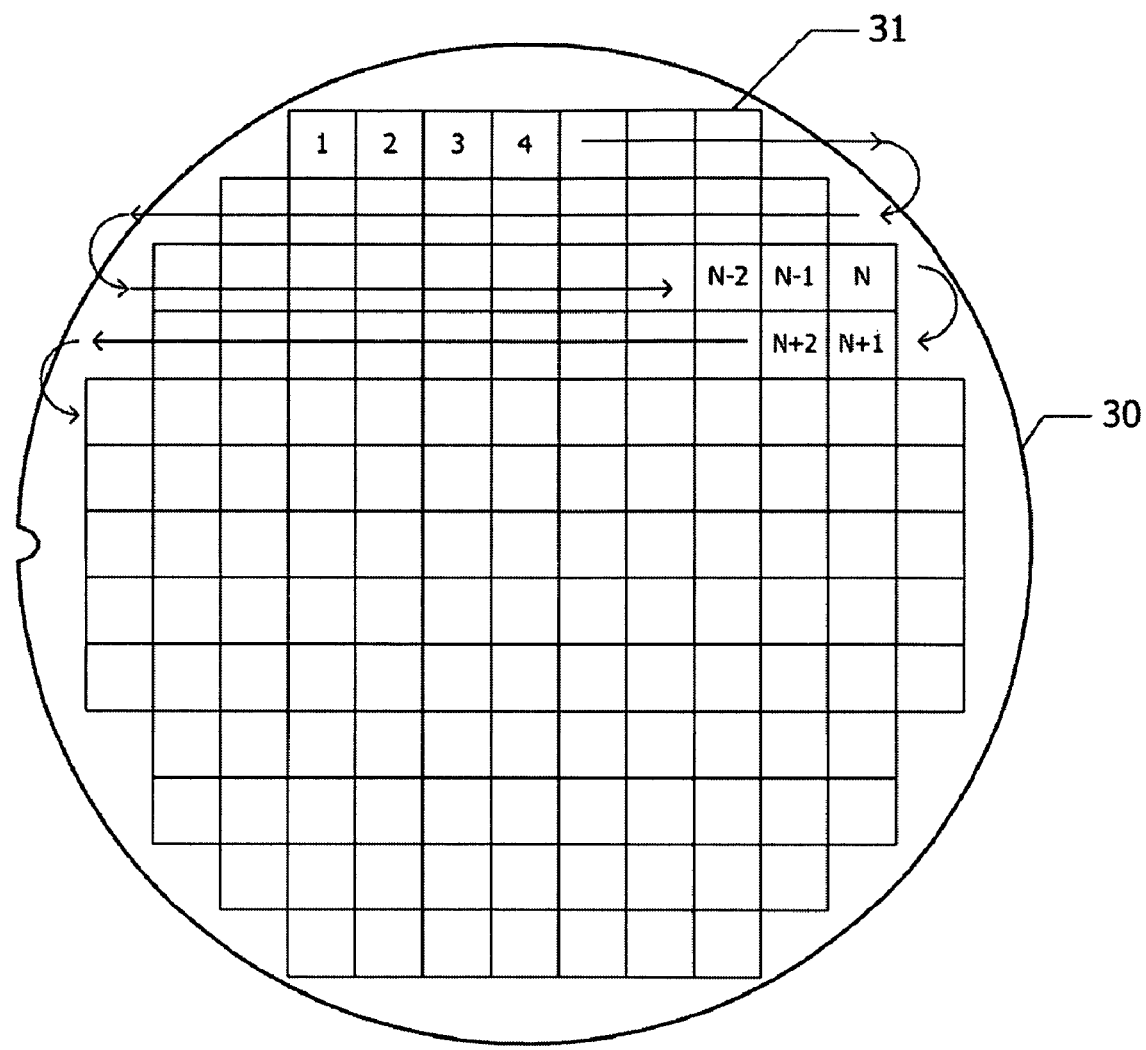
FIG. 12 is a plane view of a semiconductor wafer to be inspected according to the second embodiment.

FIG. 12 is a plan view of a semiconductor wafer 30 to be inspected with a defect inspection apparatus of the second embodiment. The surface of the semiconductor wafer 30 is partitioned into a plurality of defect inspection sections 31. Serial numbers beginning with 1 are assigned to the defect inspection sections 31. The defect detection process is executed in the order of these serial numbers. For example, if defect inspection sections 31 are distributed in a matrix shape, serial numbers are assigned sequentially from the left to right of the first row. Next, serial numbers are assigned from the right to left of the second row. In this manner, serial numbers are assigned from the left to right at odd rows, whereas serial numbers are assigned from the right to left at even rows.

The storage area 23 stores a serial number of the defect detection section 31 at which the inspection is intercepted. It is assumed that the serial number of the defect detection section 31 at which the inspection is intercepted is N. For example, the number of defect inspection sections 31 from 1 to N may be one third of the total number of defect inspection sections 31

FIG. 13 is a flow chart illustrating a defect inspection method according to the second embodiment. First, at step SE1, the defect detection process is executed from the first defect detection section 31 to N-th defect detection section 31. The defect data of detected defects are stored in the storage area 17. The defect data include serial numbers of defect detection sections 31 and position data of the defects in the defect detection section 31.

Instead of using a serial number of the defect detection section 31 as position information of intercepting the defect detection process, a row number (swath number) of the defect detection section 31 may be used. In this case, a row number is stored in the storage area 23. As in this manner, a position on the surface of the semiconductor wafer 30 may be directly designated by data stored in the storage area 23, or may be indirectly designated as another method. For example, an interception position may be defined in accordance with a ratio of the number of defect detection sections 31 to the total number of defect detection sections 31. In this case, the detection process is intercepted when the defect detection process is executed for the number of defect detection sections 31 equal to the number corresponding to the designated ratio.

An optical image of each of the detected defects is acquired at step SE2. The optical image is acquired by determining an observation position of the optical microscope 25 in accordance with position data on each of the detected defect. The acquired optical image is input to the processing unit 13.

The processing unit 13 judges whether each of the optical images has a defect in its visual field. If a defect exists, the defect is classified into a defect caused by a process trouble. If a defect is not observed in the optical image, the defect detected in an area corresponding to the optical image is classified into a pseudo defect.

At step SE3, a pseudo defect factor is calculated in each area of the first detect detection section 31 to the N-th defect detection section 31. The "pseudo defect factor" is defined as a ratio of the number of pseudo defects to a total number of defects caused by a process trouble and pseudo defects. The calculated pseudo defect factor is compared with the pseudo defect factor criterion. The pseudo defect factor criterion is stored in the storage area 24 illustrated in FIG. 11. For example, the pseudo defect factor criterion may be set to be 5%. If the pseudo defect factor is equal to or larger than the pseudo defect factor criterion, step SE4 is executed, whereas if the pseudo defect factor is smaller than the pseudo defect factor criterion, step SE7 is executed.

At Step SE4, a pseudo defect factor is calculated for each of the first to N-th defect detection sections 31, and the defect detection section 31 having the pseudo defect factor exceeding the pseudo defect factor criterion is extracted. In the following, the defect detection section whose pseudo defect factor exceeds the pseudo defect factor criterion is called a "multiple pseudo defect section". It is judged whether multiple pseudo defect sections are clustered. For example, if the three or more than three multiple pseudo defect sections are linked together in a vertical, horizontal or oblique direction, it is judged as a cluster. In other cases, it is judged that distribution is not like a cluster.

If it is judged that distribution of multiple pseudo defect sections is not like a cluster, i.e., if multiple pseudo defect sections are sparsely-distributed, it can be considered that a pseudo defect is detected as a defect because the defect detection conditions were not proper in the defect detection process at step SE1. Therefore, the defect detection conditions are modified at step SE5 and the defect detection process for the defect detection sections 31 up to the interception position is executed again returning to step SE1.

The defect detection conditions include, for example, the following. The conditions when a defect is detected in a bright field include a wavelength of a light source, a threshold value of an effective luminance of image data before a difference image is obtained, and the like. The conditions when a defect is detected in a dark field include a laser incidence angle, a laser power, a threshold value of an effective luminance of image data before a difference image is obtained, and the like.

At step SE5, a threshold value may be increased automatically to lower a sensitivity or the operator may be urged to set again the conditions.

If it is judged at step SE4 that distribution of the multiple pseudo defect sections is like a cluster, an alarm is output from the output unit 11 at step SE6, and inspection stops. If the multiple pseudo defect sections distribute like a cluster, it can be considered that a defect detection sensitivity is not improper, but the apparatus itself is defective. By outputting an alarm and stopping the inspection, it becomes possible to prevent wasteful continuation of the inspection.

If it is judged at step SE3 that the pseudo defect factor is smaller than the pseudo defect factor criterion, then at step SE7 the defect detection process starts again for the area behind the interception position, i.e., the (N+1)-th defect inspection section 31 to the defect inspection section 31 having the last serial number. After the inspection for the defect inspection section having the last serial number is completed, a Judgment process is executed at step SE8. The Judgment process at step SE8 is the same as the judgment process at step SB7 illustrated in FIG. 5.

In the second embodiment, at step SE3 the defect detection process is intercepted once in midstream, and adequacy of the defect detection process is judged based on the pseudo defect factor. As compared to the case in which it is judged that the detection process is not adequate, after the defect detection process is performed for the whole area of the semiconductor wafer 30, a wasteful process time of the defect detection apparatus can be reduced.

If it is judged at step SE3 that the pseudo defect factor is smaller than the pseudo defect factor criterion, the defect detection process resumes not from the first defect detection section 31 but from the (N+1)-th defect detection section 31. It is therefore possible to prevent duplicate execution of the defect detection process.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A defect inspection apparatus comprising:
    a first storage area for storing a distinguishing size of defect for distinguishing a pseudo defect caused by an inspection process trouble from a defect caused by a production process trouble;
    an image data acquiring unit for acquiring image data of a surface of a wafer to be inspected;
    a second storage area for storing defect data on a plurality of detected defects;
    an output unit for outputting inspection results; and
    a processing unit,
    wherein:
    the processing unit detects a defect on a wafer surface in accordance with image data acquired by the image data acquiring unit;
    stores defect data on the detected defect in the second storage area;
    compares a size of a defect detected in a partial area with the distinguishing size stored in the first storage area before a defect detection process is completed for a whole area of the wafer surface to be subjected to defect detection;
    outputs an alarm notifying that the inspection apparatus is in trouble through the output unit, if a defect having a size equal to or larger than the distinguishing size is detected and is judged as the pseudo defect; and
    executes the defect detection process for the area still not subjected to the defect detection process, if a defect having a size equal to or larger than the distinguishing size is not detected and is not judged as the pseudo defect.

2. The defect inspection apparatus according to claim 1, further comprising:
    a third storage area for storing upper limit number of pieces of defect data to be able to be stored per one wafer;
    wherein:
    the processing unit calculates an extraction upper limit number corresponding to an upper limit number of defects whose defect data are to be stored, among defects detected in a target area for the defect detection process, in accordance with a size of the target area for the defect detection process and the upper limit number stored in the third storage area; and
    if the number of detected defects exceeds the extraction upper limit number, extracts defects corresponding in number to the extraction upper limit number, from defects detected in the target area for the defect detection process; stores defect data of extracted defects in the second storage area; and discards defect data of defects not extracted.

3. The defect inspection apparatus according to claim 2, wherein:
    a surface of a wafer to be inspected is partitioned into a plurality of areas having different priority;

the defect inspection apparatus further comprises a fourth storage area for storing priority position information correlating a position on a wafer surface to a priority; and the processing unit extracts defects corresponding in number to the extraction upper limit value from detected defects, in accordance with the priority corresponding to the position of each detected defect.

4. The defect inspection apparatus according to claim 3 wherein:

the wafer surface is partitioned into a plurality of areas having different priority in such a manner that an area having a relatively dense pattern density has a higher priority than an area having a relatively coarse pattern density; and the processing unit extracts defects in such a manner that a probability of extracting a defect detected in an area having a relatively high priority is higher than a probability of extracting a defect detected in an area having a relatively low priority.

5. The detect inspection apparatus according to claim 2, wherein:

the processing unit judges based on defect data on an extracted defect whether there is a cluster defect or not; and if it is judged that there is a cluster defect, outputs an instruction of wafer bottom surface inspection, wafer circumferential invalid area inspection or bevel inspection through the output unit, in accordance with a size and position of the cluster defect.

6. A defect inspection method comprising:

detecting a defect on a wafer surface;

distinguishing a pseudo defect caused by an inspection process trouble from a defect caused by a production process trouble, for each defect detected in a partial area, in accordance with a size of each defect, before a defect detection process is completed for a whole area of the wafer surface to be subjected to defect detection;

if detected defects include a defect judged as the pseudo defect, stopping the defect detection process; and if detected defects do not include a defect judged as the pseudo defect, executing detecting a defect on the wafer surface, for an area still not subjected to the defect detection process.

7. A manufacture method for a semiconductor device, comprising:

forming an electronic circuit pattern on a surface of a semiconductor wafer;

detecting a defect on the surface of the semiconductor wafer formed with the electronic circuit pattern;

distinguishing a pseudo defect caused by an inspection process trouble from a defect caused by a production process trouble, for each defect detected in a partial area, in accordance with a size of each defect, before a defect detection process is completed for a whole area of the wafer surface to be subjected to defect detection;

if detected defects include a defect judged as the pseudo defect, stopping the defect detection process; and if detected defects do not include a defect judged as the pseudo defect, executing detecting a defect on the wafer surface, for an area still not subjected to the defect detection process.

8. A defect inspection apparatus comprising:

a first storage area for storing a position information for intercepting a defect detection process, on a surface of a wafer to be inspected;

an image data acquiring unit for acquiring image data of a surface of a wafer to be inspected;

a second storage area for storing defect data on a plurality of detected defects;

an output unit for outputting inspection results;

a processing unit; and a third storage area for storing a pseudo defect factor criterion, wherein a plurality of defect detection sections each being a unit of acquiring the image data are defined on the surface of the wafer to be inspected, and wherein:

the processing unit acquiring image data through the image data acquiring unit up to an interception position defined by the position information stored in the first storage area;

detects a defect on the wafer surface in accordance with the image data;

storing defect data of detected defects in the second storage area;

classifies detected defects into a defect caused by a production process trouble and a pseudo defect caused by an inspection process trouble, and judges based on classification results whether the defect detection process is resumed for an area behind the interception position;

compares a ratio of the number of pseudo defects to the total number of detected defects with the pseudo defect factor criterion stored in the third storage area;

judges based on comparison results whether the defect detection process is resumed for an area behind the interception position;

obtains the ratio of the pseudo defect of each of the defect detection sections if the ratio of the pseudo defect is equal to or larger than the pseudo defect factor criterion; and output an alarm through the output unit if defect detection sections having the ratio of the pseudo defect equal to or larger than the pseudo defect factor criterion distribute like a cluster.

9. The defect inspection apparatus according to claim 8, further comprising:

an optical microscope for acquiring an optical image of the wafer surface to be inspected, wherein:

the processing unit acquires an optical image at a defect detection position through the optical microscope, in accordance with position information of a detected defect; and classifies the detected defect into a defect caused by the production process trouble and a pseudo defect caused by the inspection process trouble, in accordance with the optical image.

10. The defect inspection apparatus according to claim 8, wherein if defect detection sections having the ratio of the pseudo defect equal to or larger than the pseudo defect factor criterion do not distribute like a cluster, the processing unit modifies defect detection conditions to execute again the defect detection process for an area up to the interception position.

11. A defect inspection method comprising:

detecting a defect in an area of a wafer surface up to an interception position;

classifying detected defects into a defect caused by a production process trouble and a pseudo defect caused by an inspection process trouble, in accordance with optical images at positions of the detected defects up to the interception position; and comparing a ratio of the number of pseudo defects to the total number of defects detected up to the interception position with a pseudo defect factor criterion, wherein a plurality of defect detection sections each being a unit of acquiring the image data are defined on the surface of the wafer to be inspected, and the method further comprising:

obtaining a ratio of the pseudo defect of each of the defect detection sections if the ratio of the pseudo defect is equal to or larger than the pseudo defect factor criterion; and outputting an alarm through an output unit if defect detection sections having the ratio of the pseudo defect equal to or larger than the pseudo defect factor criterion distribute like a cluster.

12. A manufacture method for a semiconductor device comprising:

forming an electronic circuit pattern on a surface of a semiconductor wafer;

detecting a defect in an area of a wafer surface formed with the electronic circuit pattern up to an interception position;

classifying detected defects into a defect caused by a production process trouble and a pseudo defect caused by an inspection process trouble, in accordance with optical images at positions of the detected defects up to the interception position; and comparing a ratio of the number of pseudo defects to the total number of defects detected up to the interception position with a pseudo defect factor criterion, wherein a plurality of defect detection sections each being a unit of acquiring the image data are defined on the surface of the wafer to be inspected, and the method further comprising:

obtaining a ratio of the pseudo defect of each of the defect detection sections if the ratio of the pseudo defect is equal to or larger than the pseudo defect factor criterion; and outputting an alarm through an output unit if defect detection sections having the ratio of the pseudo defect equal to or larger than the pseudo defect factor criterion distribute like a cluster.

* * * * *